United States Patent
Squiquera et al.

(10) Patent No.: US 11,331,378 B2
(45) Date of Patent: May 17, 2022

(54) PROPHYLACTIC PROTECTION AGAINST VIRAL INFECTIONS

(71) Applicant: Tamir Biotechnology, Inc., Short Hills, NJ (US)

(72) Inventors: Luis Squiquera, Buenos Aires (AR); Thomas Hodge, Athens, GA (US); Jamie Sulley, La Jolla, CA (US)

(73) Assignee: ORGENESIS INC., Germantown, MD (US)

( * ) Notice: Subject to any disclaimer, the term of this patent is extended or adjusted under 35 U.S.C. 154(b) by 0 days.

(21) Appl. No.: 16/320,785

(22) PCT Filed: Jul. 26, 2017

(86) PCT No.: PCT/US2017/043984
§ 371 (c)(1),
(2) Date: Jan. 25, 2019

(87) PCT Pub. No.: WO2018/022774
PCT Pub. Date: Feb. 1, 2018

(65) Prior Publication Data
US 2020/0179493 A1     Jun. 11, 2020

Related U.S. Application Data

(63) Continuation-in-part of application No. 15/582,133, filed on Apr. 28, 2017, now Pat. No. 10,835,598.
(Continued)

(51) Int. Cl.
*A61K 38/54*     (2006.01)
*A61K 38/46*     (2006.01)
*A61K 9/00*     (2006.01)
*A61P 31/18*     (2006.01)
*A61K 47/26*     (2006.01)
(Continued)

(52) U.S. Cl.
CPC .......... *A61K 38/465* (2013.01); *A61K 9/0014* (2013.01); *A61K 47/02* (2013.01); *A61K 47/06* (2013.01); *A61K 47/10* (2013.01); *A61K 47/16* (2013.01); *A61K 47/26* (2013.01);
(Continued)

(58) Field of Classification Search
None
See application file for complete search history.

(56) References Cited

U.S. PATENT DOCUMENTS 5,559,212 A     9/1996   Ardelt
5,728,805 A     3/1998   Ardelt
(Continued)

FOREIGN PATENT DOCUMENTS

WO     WO 2016/028634 A1     2/2016

OTHER PUBLICATIONS

Saxena et al., "Onconase and Its Therapeutic Potential," Laboratory Medicine, No. 5, vol. 34: 380-387 (Year: 2003).*
(Continued)

*Primary Examiner* — M Franco G Salvoza
(74) *Attorney, Agent, or Firm* — Mark S. Cohen; Pearl Cohen Zedek Latzer Baratz LLP

(57) ABSTRACT

The present disclosure provides methods for prophylactically treating a subject for viral infections comprising topically administering a ranpirnase composition. The disclosure also provides compositions that could be used for prophylactic treatment.

15 Claims, 5 Drawing Sheets
Specification includes a Sequence Listing.

Related U.S. Application Data

(60) Provisional application No. 62/367,050, filed on Jul. 26, 2016.

(51) Int. Cl.
  *A61K 47/38* (2006.01)
  *A61K 47/16* (2006.01)
  *A61K 47/02* (2006.01)
  *A61K 47/06* (2006.01)
  *A61K 47/10* (2017.01)

(52) U.S. Cl.
  CPC .............. *A61K 47/38* (2013.01); *A61P 31/18* (2018.01); *C12Y 301/27* (2013.01)

(56) References Cited

U.S. PATENT DOCUMENTS

| | | | |
|---|---|---|---|
| 6,239,257 B1 | 5/2001 | Ardelt | |
| 7,229,824 B2 | 6/2007 | Saxena | |
| 8,333,971 B2* | 12/2012 | Goldenberg | A61K 47/6809 424/178.1 |
| 2004/0072910 A1* | 4/2004 | Porat | A61K 31/366 514/635 |
| 2010/0012132 A1* | 1/2010 | Harrison | A61Q 19/00 128/844 |
| 2012/0121569 A1 | 5/2012 | Saxena et al. | |
| 2013/0022589 A1 | 1/2013 | Saxena et al. | |

OTHER PUBLICATIONS

Ilinskaya et al., "Ribonucleases as Antiviral Agents," Molecular Biology, vol. 48, No. 5: 615-623 (Year: 2014).*
Markel et al., "Sexually transmitted diseases," Prim Care 40(3): 557-87 (Year: 2013).*
Gray et al., "Approaches to Preventative and Therapeutic HIV vaccines," Curr Opin Virol 17: 104-109 (Year: 2016).*
FDA CDER, "Guidance for Industry: Vaginal Microbicides: Development for the Prevention of HIV Infection," Office of Communications, FDA, U.S. Department of Health and Human Services, available at https://www.fda.gov/media/85288/download (Year: 2016).*
Saxena et al., "Inhibition of HIV-1 Production and Selective Degradation of Viral RNA by an Amphibian Ribonuclease," Journal of Biological Chemistry, vol. 271, No. 34: 20783-20788 (Year: 1996).*
Merriam-Webster "Treat", found online at https://www.merriam-webster.com/dictionary/treat (Year: 2020).*
Merriam-Webster "Prophylactic", found online at https://www.merriam-webster.com/thesaurus/prophylactic (Year: 2020).*
Chang et al. "Generic development of topical dermatologic products: formulation development, process development, and testing of topical dermatologic products" The AAPS journal. Jan. 1, 2013;15(1):41-52.
Holt et al. "The sheep as a model of preclinical safety and pharmacokinetic evaluations of candidate microbicides" Antimicrobial agents and chemotherapy. Jul. 1, 2015;59(7):3761-70.
International Search Report for PCT Application No. PCT/US2017/043984 dated Oct. 10, 2017.
Youle et al. "RNase inhibition of human immunodeficiency virus infection of H9 cells" Proceedings of the National Academy of Sciences. Jun. 21, 1994;91(13):6012-6.

* cited by examiner

SEQUENCE LISTING

```
<160> NUMBER OF SEQ ID NOS: 4

<210> SEQ ID NO 1
<211> LENGTH: 104
<212> TYPE: PRT
<213> ORGANISM: Rana pipiens

<400> SEQUENCE: 1

Glu Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Ala Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100

<210> SEQ ID NO 2
<211> LENGTH: 104
<212> TYPE: PRT
<213> ORGANISM: Rana pipiens

<400> SEQUENCE: 2
```

Glu Asp Trp Leu Thr Phe Gln Lys Lys His Val Asn Thr Arg Asp
1               5                   10                  15

Val Asp Cys Asn Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
            85                  90                  95

His Phe Val Gly Val Gly Arg Cys
            100

<210> SEQ ID NO 3
<211> LENGTH: 114
<212> TYPE: PRT
<213> ORGANISM: Rana pipiens

<400> SEQUENCE: 3

Lys Pro Lys Glu Asp Arg Glu Trp Glu Lys Phe Lys Thr Lys His Ile
1               5                   10                  15

Thr Ser Gln Ser Val Ala Asp Phe Asn Cys Asn Arg Thr Met Asn Asp
            20                  25                  30

Pro Ala Tyr Thr Pro Asp Gly Gln Cys Lys Pro Ile Asn Thr Phe Ile
            35                  40                  45

His Ser Thr Thr Gly Pro Val Lys Glu Ile Cys Arg Arg Ala Thr Gly
50                  55                  60

Arg Val Asn Lys Ser Ser Thr Gln Gln Phe Thr Leu Thr Thr Cys Lys
65                  70                  75                  80

Asn Pro Ile Arg Cys Lys Tyr Ser Gln Ser Asn Thr Thr Asn Phe Ile
            85                  90                  95

Cys Ile Thr Cys Arg Asp Asn Tyr Pro Val His Phe Val Lys Thr Gly
            100                 105                 110

Lys Cys

<210> SEQ ID NO 4
<211> LENGTH: 115
<212> TYPE: PRT
<213> ORGANISM: Rana pipiens

<400> SEQUENCE: 4

Met Lys Pro Lys Glu Asp Arg Glu Trp Glu Lys Phe Lys Thr Lys His
1               5                   10                  15

Ile Thr Ser Gln Ser Val Ala Asp Phe Asn Cys Asn Arg Thr Met Asn
            20                  25                  30

Asp Pro Ala Tyr Thr Pro Asp Gly Gln Cys Lys Pro Ile Asn Thr Phe
            35                  40                  45

Ile His Ser Thr Thr Gly Pro Val Lys Glu Ile Cys Arg Arg Ala Thr
50                  55                  60

Gly Arg Val Asn Lys Ser Ser Thr Gln Gln Phe Thr Leu Thr Thr Cys
65                  70                  75                  80

Lys Asn Pro Ile Arg Cys Lys Tyr Ser Gln Ser Asn Thr Thr Asn Phe
            85                  90                  95

-continued

```
Ile Cys Ile Thr Cys Arg Asp Asn Tyr Pro Val His Phe Val Lys Thr
            100                 105                 110

Gly Lys Cys
        115
```

PROPHYLACTIC PROTECTION AGAINST VIRAL INFECTIONS

CROSS REFERENCE TO RELATED APPLICATIONS

This application is a 371 national stage entry of International Application No. PCT/US2017/043984, filed Jul. 26, 2017, which claims priority to U.S. Provisional Application No. 62/367,050, filed Jul. 26, 2016 and is a continuation-in-part of U.S. patent application Ser. No. 15/582,133, filed Apr. 28, 2017, the contents of which are hereby incorporated in full for all purposes.

FIELD OF THE DISCLOSURE

The present disclosure relates to prophylactic treatment of viral infections using compositions comprising ribonucleases. More particularly, the disclosure relates to prophylactic treatment of sexually-transmitted viral infections, such as HIV and HPV infections, using topical ranpirnase compositions.

CROSS REFERENCE TO DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: TAMI_016_01 WO_SeqList_ST25.txt, date recorded: Jul. 20, 2017, file size: 8 kilobytes).

BACKGROUND

Sexually transmitted infections, and particularly HIV, pose a significant public health threat. At present, individuals wishing to protect themselves against such infections rely upon mechanical measures (such as condoms and dental dams) to prevent them from coming into contact with their partner's bodily fluids, which may contain HIV. These measures are not optimal because some individuals are reluctant to use them. Recently, the use of orally administered antiretrovirals (e.g. tenofovir) has been proposed as pre-exposure prophylactic treatment. While oral prophylaxis is effective, it suffers from significant disadvantages. Oral prophylaxis must be used consistently for a prolonged period and its effectiveness is reduced or even eliminated if the patient is not fully compliant. Other oral medications can adversely affect the efficacy of oral prophylaxis. Furthermore, oral prophylactic medications are associated with side effects such as nausea and/or diarrhea.

Accordingly, there is a need for the development of prophylactic measures that are easy to use and not associated with side effects such as nausea and/or diarrhea.

SUMMARY OF THE DISCLOSURE

The present disclosure provides antiviral prophylactic measures that do not require injection or oral administration of a prophylactic agent.

The present disclosure provides methods for prophylactically treating a subject for sexually-transmitted viral infections using ribonuclease compositions applied topically and compositions containing ribonucleases.

In one embodiment, the method for prophylactically treating a subject from contracting a sexually-transmitted viral infection comprises topically applying a composition comprising a ribonuclease and pharmaceutically acceptable excipients.

In one embodiment, the ribonuclease is a member of the ribonuclease A superfamily and is selected from the group consisting of: ranpirnase, the '805 variant, Amphinase 2, and rAmphinase 2.

In some embodiments, the composition for prophylactic treatment comprises a personal lubricant.

In some embodiments, the composition for prophylactic treatment is a gel, cream, ointment, lotion, solution, suspension, or a spray.

In one embodiment, the composition for prophylactic treatment comprises an effective amount of a ribonuclease and glycerin, hydroxyethylcelluose, chlorhexidine gluconate, gluconolactone, methylparaben, and sodium hydroxide (e.g., KY-Jelly®).

In one embodiment, the composition for prophylactic treatment comprises an effective amount of a ribonuclease and glycerin, propylene glycol, sorbitol, hydroxyethylcelluose, benzoic acid, methylparaben, and sodium hydroxide.

In certain embodiments, the ribonuclease is present in the composition in an amount from about 0.01% by weight to about 10% by weight, based on the total weight of the composition. In certain other embodiments, the ribonuclease is present in the composition in an amount from about 0.1% by weight to about 1% by weight, based on the total weight of the composition. In some embodiments, the ribonuclease is present in the composition in an amount of about 1%, about 5%, or about 10%, by weight, based on the total weight of the composition. In particular embodiments, the range is between about 1% and about 10%, by weight.

The methods of the present disclosure comprise applying the ribonuclease composition prior to or during sexual intercourse. In particular aspects, the composition may be applied one to five times a day.

The composition may be applied topically to body regions that are exposed to sexually-transmitted viruses.

The compositions and methods of the present disclosure protect subjects from contracting sexually-transmitted viruses such as herpes simplex viruses (HSV), human papillomaviruses (HPV), human immunodeficiency virus (HIV), hepatitis B and C virus, and cytomegalovirus.

BRIEF DESCRIPTION OF THE DRAWINGS

FIG. 2A. Explants were co-exposed to $1 \times 10^5$ virons/mL HIV-1 Bal and drug for 2 hours. Supernatant was collected for a 14 day culture period and assayed for p24 levels using the AlphaLISA Kit, (N=6 individuals with 3 biopsies each). Statistical significance was determined using standard mixed effect model model with $p<0.05$.

DETAILED DESCRIPTION

Figure 1:
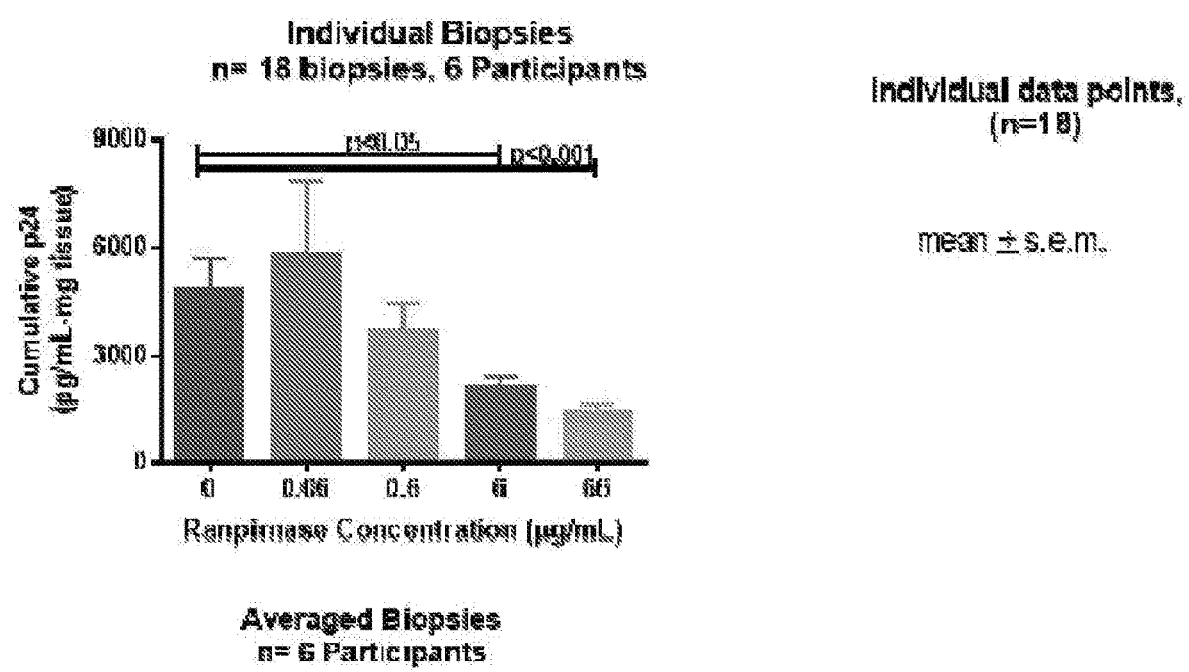
FIG. 1 is a graph showing the cumulative HIV infection of individual rectal tissue biopsies at 14 days as a function of ranpirnase concentration using an explant challenge model.

The present disclosure is based, in part, on the discovery that pre-treatment of a subject using compositions comprising a ribonuclease can protect the subject from acquiring sexually-transmitted viral infections. Accordingly, the present disclosure provides methods for prophylactically treating a subject from contracting a sexually-transmitted viral infection. The subject is a mammal, in particular, human.

In one embodiment, the method for a prophylactic treatment comprises topically applying a composition comprising a ribonuclease and pharmaceutically acceptable excipients. The ribonuclease composition can be in the form of a gel, liquid, cream, ointment, lotion, solution, suspension, or a spray. These pharmaceutical forms have been defined by US Pharmacopeia (www.usp.org/sites/default/files/usp_pdf/EN/USPNF/transdennalStimArticle.pdf) which is incorporated by reference for all purposes and particular the formulations of gels, liquids, creams, ointments, lotions, solutions, and sprays as defined therein. Further descriptions on the development of generic transdermal product have been described by Chang et al. (Chang, Raw, A., Lionberger, R., & Yu, L. (2013). Generic Development of Topical Dermatologic Products: Formulation Development, Process Development, and Testing of Topical Dermatologic Products. *The AAPS Journal*, 15(1), 41-52.

In one embodiment, the ribonuclease is ranpirnase. Ranpirnase is an RNase isolated from oocytes of the leopard frog *Rana pipiens* which is disclosed in U.S. Pat. No. 5,559,212, and is also known as Onconase®. The amino acid sequence of ranpirnase is provided in SEQ ID NO: 1. Ranpirnase has been tested and found to be cytotoxic to cancer cells because of its enzymatic activity against RNA.

A variant of ranpirnase is disclosed in U.S. Pat. No. 5,728,805 (hereinafter, the "'805 variant"). The '805 variant is also an RNase, and has likewise been found to be cytotoxic to certain cancer cells. The '805 variant is a close variant of ranpirnase; its amino acid sequence is identical to that of ranpirnase except that it has valine instead of isoleucine at position 11, asparagine instead of aspartic acid at position 20, and arginine instead of serine at position 103 of the ranpirnase amino acid sequence. In some embodiments, the '805 variant is referred to as "Val11, Asn20, Arg103-Ranpirnase". The amino acid sequence of the '805 variant is provided in SEQ ID NO: 2.

Amphinase 2 is also an RNase. It is the protein identified as 2325p4 in U.S. Pat. No. 6,239,257 and it also has been found to be cytotoxic to cancer cells. The amino acid sequence of Amphinase 2 is provided in SEQ ID NO: 3.

Recombinant Amphinase 2 ("rAmphinase 2") is similar to Amphinase 2, but has a Met residue at position −1 and lacks glycan moieties that are located in Amphinase 2 at positions 27 and 91. rAmphinase 2 is described in U.S. Pat. No. 7,229,824. The amino acid sequence of rAmphinase 2 is provided in SEQ ID NO: 4.

In certain embodiments, the composition comprises a ribonuclease may use a personal lubricant as a vehicle to deliver and stabilise the ribonuclease. The term "personal lubricant" maybe used interchangeably with the term "sexual lubricant" throughout this disclosure. The personal lubricant compositions comprising a ribonuclease can be in the form of a gel, liquid, cream, ointment, lotion, solution, suspension, or a spray.

A number of brands of personal lubricants are known, for example, K-Y jelly, Astroglide, Durex Play, Sylk, Elbow Grease, Good Clean Love, Gynol II, ID Glide Ultra, PRE, Replens, Slippery Stuff and Sliquid Organic, etc. The present disclosure provides personal lubricants that comprise a ribonuclease.

In one embodiment, the personal lubricant comprises ranpirnase or other ribonucleases and glycerol and/or a cellulose derivative. The cellulose derivative may include hydroxyethyl cellulose, sodium carboxymethyl cellulose and/or cellulose polymer.

In one embodiment, the personal lubricant comprises ranpirnase and one or more excipients selected from the group consisting of water, glycerin, propylene glycol, sorbitol, ethers or esters of cellulose such as hydroxyethylcelluose, dimethicone, cyclomethicone, dimethicone/vinyl dimethicone crosspolymer, vegetable oil, PEG/PPG-18/18 Dimethicone, Propanediol, Sodium Chloride, 1,2-Hexanediol, Dimethiconol, Caprylhydroxamic Acid, Caprylyl Glycol, lactic acid, chlorhexidine gluconate, gluconolactone, methylparaben, propyl paraben, benzoic acid, Polyquaternium 15, and sodium hydroxide.

In one embodiment, the personal lubricant comprises ranpirnase and a water-based personal lubricant comprising one or more excipients selected from the group consisting of water, glycerin, propylene glycol, sorbitol, ethers or esters of cellulose such as hydroxyethylcelluose, chlorhexidine gluconate, gluconolactone, parabens such as methylparaben and propylparaben, benzoic acid, Polyquaternium 15, and sodium hydroxide.

In another embodiment, the personal lubricant comprises ranpirnase and a silicone-based personal lubricant comprising one or more excipients selected from the group consisting of dimethicone, cyclomethicone, dimethicone/vinyl dimethicone crosspolymer, and vegetable oil including coconut oil, olive oil, etc.

In yet another embodiment, the personal lubricant comprises ranpirnase and a hybrid lubricant that combines excipients of a water-based lubricant and a silicone-based ingredients. In one embodiment, such hybrid lubricant comprises Glycerin, Dimethicone, Purified Water, Cyclomethicone, PEG/PPG-18118 Dimethicone, Propanediol, Sodium Chloride, 1,2-Hexanediol, Dimethiconol, Caprylhydroxamic Acid, and Natural Flavors.

In one embodiment, the personal lubricant comprises ranpirnase and pharmaceutically acceptable excipients selected from the group consisting of water, glycerin, ethers or esters of cellulose such as hydroxyethylcelluose, chlorhexidine gluconate, gluconolactone, methylparaben, and sodium hydroxide. In another embodiment, the personal lubricant comprises ranpirnase and pharmaceutically acceptable excipients selected from the group consisting of water, glycerin, propylene glycol, sorbitol, hydroxyethylcelluose, benzoic acid, methylparaben, and sodium hydroxide, as pharmaceutically acceptable excipients.

In yet another embodiment, the personal lubricant comprises ranpirnase and pharmaceutically acceptable excipients selected from the group consisting of Glycerin, Propylene Glycol, Polyquaternium 15, Methylparaben, and Propylparaben.

In yet another embodiment, the personal lubricant comprises ranpirnase and pharmaceutically acceptable excipients selected from the group consisting of dimethicone, cyclomethicone, dimethicone/vinyl dimethicone crosspolymer, and a vegetable oil such as coconut oil, olive oil, etc. In yet another embodiment, the personal lubricant comprises ranpirnase and pharmaceutically acceptable excipients selected from the group consisting of dimethicone and cyclomethicone.

In yet another embodiment, the personal lubricant comprises ranpirnase and pharmaceutically acceptable excipients selected from the group consisting of Glycerin, Dimethicone, Purified Water, Cyclomethicone, PEG/PPG-18/18 Dimethicone, Propanediol, Sodium Chloride, 1,2-Hexanediol, Dimethiconol, Caprylhydroxamic Acid, and Natural Flavors.

In yet another embodiment, the personal lubricant comprises ranpirnase and pharmaceutically acceptable excipients selected from the group consisting of Purified Water, Propylene Glycol, Hydroxyethylcellulose, Caprylyl Glycol, Caprylhydroxamic Acid, Propanediol, Polyquaternium 15, and Lactic Acid.

The methods for prophylactically treating a subject from contracting a sexually-transmitted viral infection comprise topically applying any one of compositions describe above.

Figure 2A:
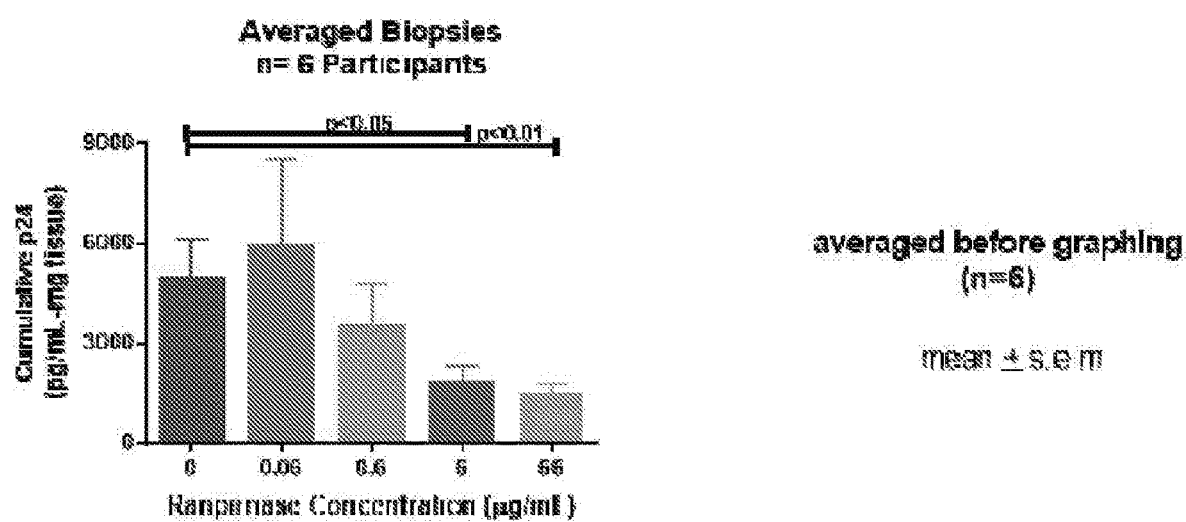
FIG. 2A is a graph showing the cumulative averaged HIV infection of 5 rectal tissue biopsy triplets as a function of ranpirnase concentration. Specifically, dose-dependent reduction in Day 14 cumulative p24 release from HIV-1Bal infected biopsies without toxicity by ranpirnase.
Figure 2B:
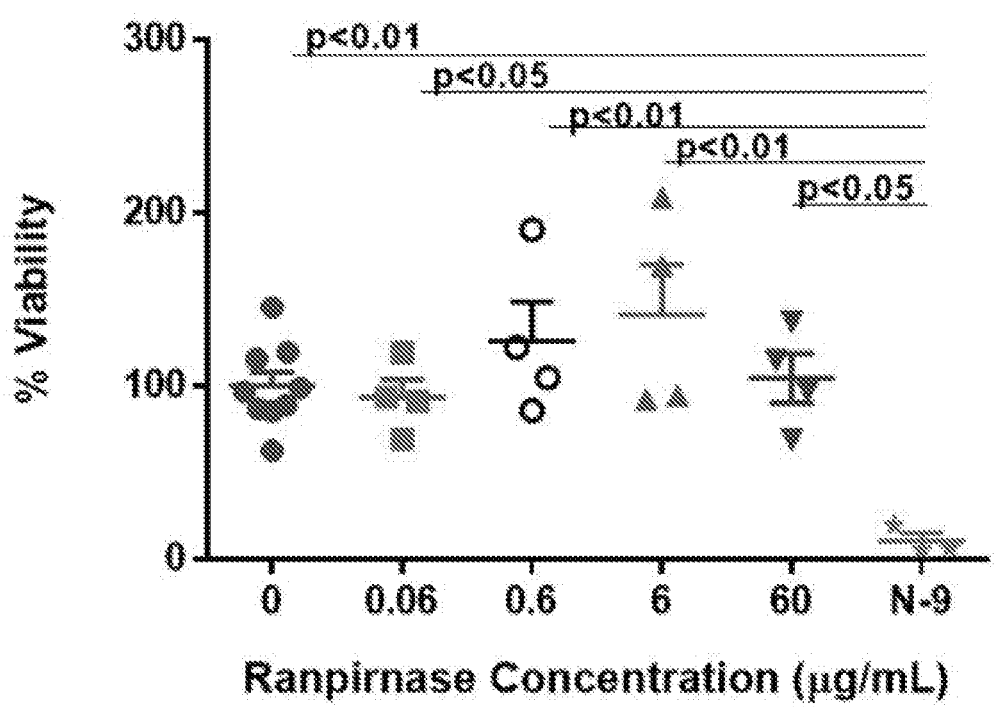
FIG. 2B shows explant viability analysis. Explants were incubated for 2 hours in the presence of drug prior to viability analysis by MTT. Data are presented as percent viability relative to control biopsies not exposed to drug. N-9 is positive control, included to ensure proper assay function. Data are presented as mean+/−s.e.m (N=3-9). Statistical significance was determined using standard mixed effect model with $p<0.05$.

In some embodiments, the ribonuclease is present in the composition at a concentration of about 0.1 mg/mL to about 10 mg/mL, such as, about 0.1, 0.2, 0.3, 0.4, 0.5, 0.6, 0.7, 0.8, 0.9, 1.0, 2, 3, 4, 5, 6, 7, 8, 9, or 10 mg/mL, including values and ranges therebetween. Preferably and advantageously with respect to a combination of efficacy and viability, however, the concentration range is lower. Such lower concentrations are particularly preferred when the ribonuclease is ranpirnase. See FIGS. 2A and 2B Suitably low concentrations include where the ribonuclease is present in a range of about 2 to about 200 µg/ml, preferably, about 5 µg/ml to about 100 µg/ml and most preferably about 5 µg/ml to about 50 µg/ml. As used herein, the term "about" represents a 10% variance of the indicated value, unless otherwise specified as +/−20%. Ranpirnases in these concentrations does not result in decreased host cell viability. Thus, in preferable aspects, the host cell viability, remains about 100%. See FIG. 2B.

In some other embodiments, the ribonuclease is present the composition at a concentration of about 0.1% to about 10% w/w, such as, about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% w/w, including values and ranges therebetween. For example, the ribonuclease may be present in the composition at a concentration of about 1% to about 10%, about 0.5% to about 5%, about 1% to about 5%, or about 5% to about 10% w/w, including values and ranges therebetween.

In yet some other embodiments, the ribonuclease is present in the composition at a concentration of about 0.1% to about 10% w/v, such as, about 0.1%, 0.2%, 0.3%, 0.4%, 0.5%, 0.6%, 0.7%, 0.8%, 0.9%, 1.0%, 2%, 3%, 4%, 5%, 6%, 7%, 8%, 9%, or 10% w/v, including values and ranges therebetween.

In certain embodiments, a method for prophylactically treating a subject for sexually-transmitted viral infections comprises transfecting a gene encoding ranpirnase or other ribonucleases in a bacterium and administering the transfected bacterium to a subject. For example, *E. coli* and *Lactobacillus* are part of normal microbial flora residing in mucosal tissues such as vagina and rectum. A gene or a DNA sequence encoding ranpirnase or other ribonucleases can be transfected into *E. coli* or *Lactobacillus* and the transfected/modified *E. coli* or *Lactobacillus* are introduced into the subject. The modified *E. coli* or *Lactobacillus* would enter the mucosal tissues of the subject and produce ranpirnase.

Alternatively, other bacteria could be used to prophylactically protect other tissues against other viral infections. For example, probiotic *E. coli* comprising transfected ranpirnase DNA could be used to protect against viral infections of the digestive tract. Similarly, modified saprophytic *Streptococci* could be delivered to protect a subject's external genitalia against HIV.

Figure 4:
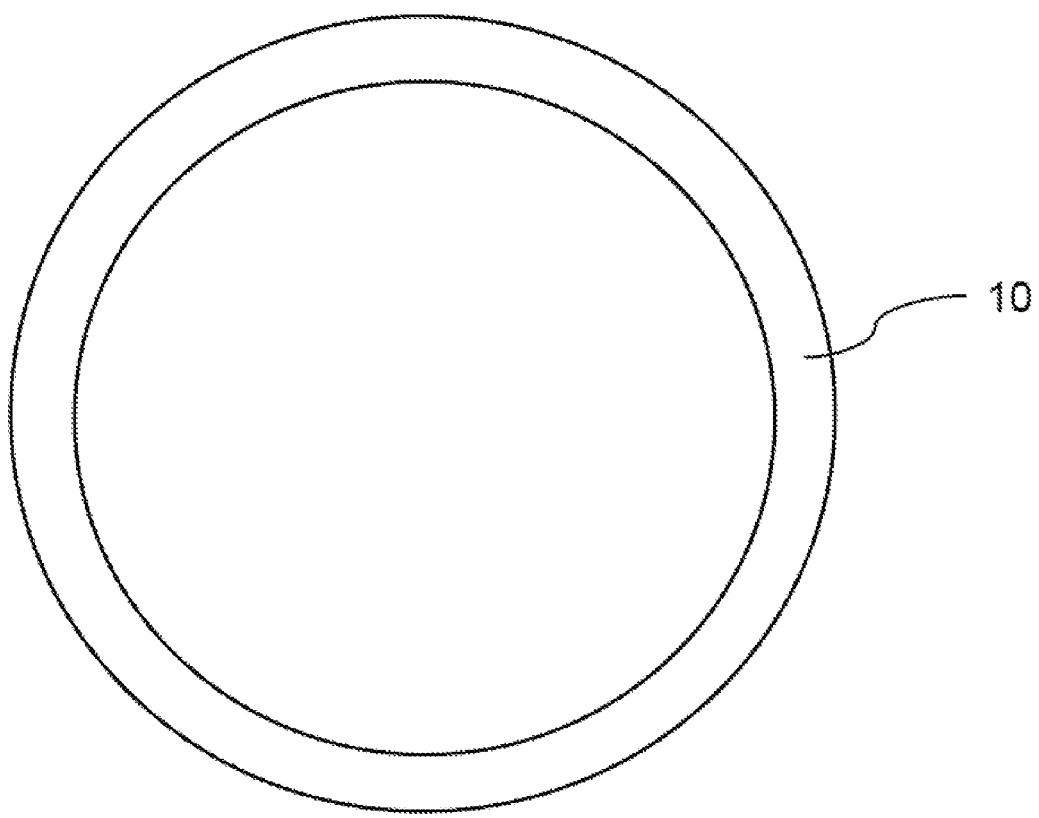
FIG. 4 shows a vaginal ring such as would be used in one of the embodiments of the invention.

In certain other embodiments, the present disclosure provides an intravaginal ring 10 (FIG. 4) made of a suitably porous and biocompatible material that is impregnated with ranpirnase other suitable ribonucleases. Intravaginal rings are known and are used to deliver birth control drugs as well as dapivirine (a candidate microbicide). The composition of such a ring is disclosed in Holt, et al., Antimicrobial Agents and Chemotherapy, Vol. 59, No. 7, pp. 3761-3770 (July, 2015).

When the intravaginal ring impregnated with ranpirnase is inserted into the vagina, the ranpirnase is released and would confer protection against viral infections. The ranpirnase may be mixed with other agents, e.g. dispersing agents, prior to applying to the intravaginal rings.

The prophylactic treatment methods of the present disclosure protect subjects from sexually-transmitted viral infections. In certain embodiments, the prophylactic treatment methods protect subjects from infections caused by a virus selected from the group consisting of herpes simplex viruses (HSV), human papillomaviruses (HPV), human immunodeficiency virus (HIV), hepatitis B and C virus, and cytomegalovirus. Thus, in particular aspects, HIV infection in normal cells from rectal explants is inhibited after incubation with concentrations or ranpirnase ranging from 6 μg/ml to 66 μg/ml. Thus, in particular aspects, the compositions disclosed herein, while applied to the surface of the cell, allow penetration of ribonuclease (e.g., ranpirnase) into the cell where the HIV, or other viral RNA, is degraded, thus preventing the infection from establishing a foothold in the cell. The prophylactic treatment methods of the present disclosure may protect subjects from acquiring sexually-transmitted diseases such as Acquired Immunodeficiency Syndrome (AIDS), anal warts, and genital warts.

The prophylactic treatment is intended to be administered topically, i.e. to a surface of the patient's body such as the skin or mucous membranes. Preferably, the composition is administered to the patient's skin, in particular, in body regions that are exposed to sexually-transmitted viruses. The topical administration according to the present invention includes vaginal, extra-vaginal (outside of the vagina), intravaginal (inside the vagina), anal, peri-anal (surrounding the anus) and intra-anal (inside the anus) administration.

The composition may be applied topically prior to or during the exposure to sexually-transmitted viruses, e.g., prior to or during sexual intercourse.

The compositions of the present disclosure may be applied multiple times during the day. For example, in one embodiment, the prophylactic treatment comprises topically applying the ranpirnase compositions once, twice, three times, four times, five times, six times, seven times, eight times, nine times, or ten times in a day.

This disclosure is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the disclosure.

All patent and non-patent documents referenced throughout this disclosure are incorporated by reference herein in their entirety for all purposes.

EXAMPLES

Example 1

Three rectal tissue explants were obtained from six healthy volunteers (three from each volunteer). Fifteen explants were used to test the prophylactic effect of ranpirnase against HIV and three explants were used in an MIT assay to check whether ranpirnase caused cellular toxicity.

To test the prophylactic effect of ranpirnase against HIV, five solutions were prepared as follows:

1. $10^5$ TCID$_{50}$ of HIV-1$_{BaL}$ together with 0.06 μg/mL ranpirnase (test),
2. $10^5$ TCID$_{50}$ of HIV-1$_{BaL}$ together with 0.6 μg/mL ranpirnase (test),
3. $10^5$ TCID$_{50}$ of HIV-1$_{BaL}$ together with 6 μg/mL ranpirnase (test),
4. $10^5$ TCID$_{50}$ of HIV-1$_{BaL}$ together with 66 μg/mL ranpirnase (test), and
5. $10^5$ TCID$_{50}$ of HIV-1$_{BaL}$ with no ranpirnase (control).

The fifteen tissue explants were arranged into five groups of three. Each group of explants was incubated for two hours with one of the mixtures. The tissue explants were then washed multiple times and cultured at 37° C. and 5% $CO_2$ for fourteen days. Supernatants were collected on Days 3, 7, 10, and 14. The culture medium was prepared using equal parts of complete RMPI and Zosyn® 50 mg/mL. 500 mL of complete RMPI were prepared by mixing:

90% RPMI 1640—445 mL,

10% Fetal Bovine Serum—50 mL, and

1% Antibiotic/Antimycotic 5—5.0 mL.

Figure 3:
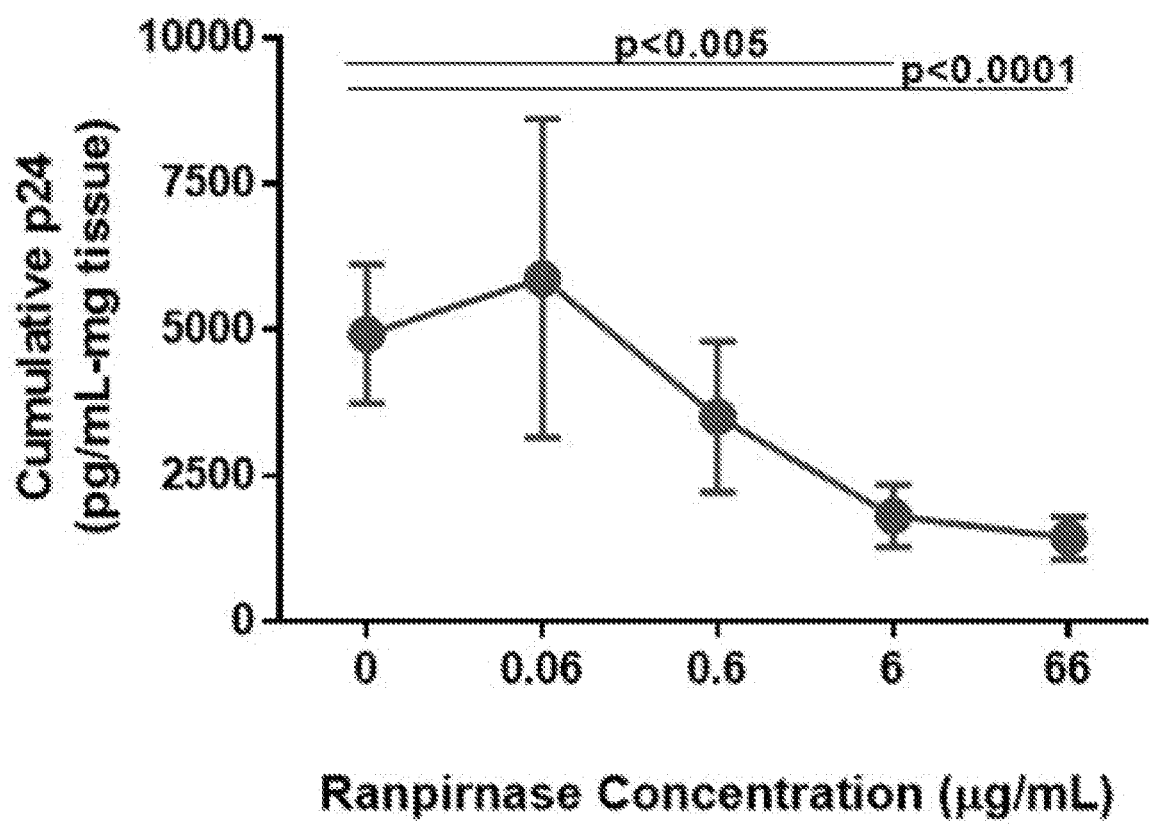
FIG. 3 is a graph displaying the data in FIG. 2 in a different format to clearly show the standard error of the mean at each ranpirnase concentration.

The severity of HIV infection of the tissue explants was determined by assaying the supernatant for HIV-1 p24 antigen using the AlphaLISA platform. The efficacy endpoint was the tissue explant weight adjusted Day 14 cumulative HIV-1 p24. As shown in FIGS. 1-3, increasing concentration of ranpirnase caused a dose dependent reduction in HIV-1 p24 antigen in the tissue explants. The statistical significance values (p values) are shown in FIGS. 1-3; whether the values were averaged or not, the results for 0.00 μg/mL, 0.06 μg/mL, and 0.6 μg/mL of ranpirnase were below the 5% level of significance. And, the results for 6.00 μg/mL and 66 μg/mL of ranpirnase were below the 1% level of significance when the results of each group of three tissue explants were averaged, and below the 0.1% level of significance when the results of each tissue explant is taken individually.

In each of FIGS. 1-3, the standard error of the mean is also shown by the vertical lines shown by themselves in FIG. 3 and superposed on the bars in Figures. 1 and 2.

Three tissue explants exposed to ranpirnase alone were tested for cell viability using in an MIT assay. The results of the assay showed that ranpirnase did not induce cellular toxicity, See FIG. 2B.

This experiment showed that tissue explants exposed to ranpirnase, in particular, to the ranpirnase concentrations of 6 μg/mL and greater, developed increased resistance to HIV infection, i.e. ranpirnase had a prophylactic effect.

---

The invention claimed is:

1. A method for increasing the resistance of a subject to a sexually-transmitted viral infection, wherein the sexually transmitted viral infection is human immunodeficiency virus (HIV) infection, the method comprising topically applying a composition comprising an unconjugated ribonuclease, and optionally one or more pharmaceutically acceptable excipients, wherein the unconjugated ribonuclease is present in a concentration of 6 µg/ml and greater, and wherein said resistance is increased in the subject compared with a subject not administered said ribonuclease.

2. The method of claim 1, wherein the ribonuclease is a member of the ribonuclease A superfamily.

3. The method of claim 1, wherein the ribonuclease is selected from a group consisting of: ranpirnase, the '805 ranpirnase variant, Amphinase 2, and rAmphinase 2.

4. The method of claim 1, wherein the composition is a personal lubricant.

5. The method of claim 1, wherein the composition is a gel, cream, ointment, lotion, solution, suspension, or a spray.

6. The method of claim 1, wherein the composition comprises glycerin, hydroxyethylcellulose, chlorhexidine gluconate, gluconolactone, methylparaben, and sodium hydroxide, as pharmaceutically acceptable excipients.

7. The method of claim 1, wherein the composition comprises glycerin, propylene glycol, sorbitol, hydroxyethylcellulose, benzoic acid, methylparaben, and sodium hydroxide, as pharmaceutically acceptable excipients.

8. The method of claim 1, wherein the ribonuclease is present in an amount from about 0.01% by weight to about 10% by weight, based on the total weight of the composition.

9. The method of claim 1, wherein the ribonuclease is present in an amount from about 0.1% by weight to about 1% by weight, based on the total weight of the composition.

10. The method of claim 1, wherein the ribonuclease is present in an amount of about 1%, about 5%, or about 10%, by weight, based on the total weight of the composition.

11. The method of claim 1, wherein the composition is applied prior to or during sexual intercourse.

12. The method of claim 1, wherein the composition is applied one to five times a day.

13. The method of claim 1, wherein the composition is applied topically to body regions that are exposed to sexually transmitted viruses.

14. The method of claim 1, wherein ranpirnase is present at a concentration of about 6 µg/ml to about 66 µg/ml.

15. The method of claim 1, wherein said topical administration is selected from vaginal, extra-vaginal, intra-vaginal, anal, peri-anal and intra-anal administration.

* * * * *